United States Patent [19]

Beitner

[11] 4,092,138

[45] May 30, 1978

[54] DENTAL DESK UNIT

[75] Inventor: Shlomo Beitner, Tel-Aviv, Israel

[73] Assignee: Bipol Ltd., Tel-Aviv, Israel

[21] Appl. No.: 708,570

[22] Filed: Jul. 26, 1976

[51] Int. Cl.² ............ F25B 21/02; F25B 29/00; B26B 21/24

[52] U.S. Cl. ............................ 62/3; 165/48; 32/40 A

[58] Field of Search .............. 62/3; 165/48, 58, 170; 32/1, 39, 40 A

[56] References Cited

U.S. PATENT DOCUMENTS

| | | | |
|---|---|---|---|
| 2,973,627 | 3/1961 | Lackey et al. | 62/3 |
| 3,230,723 | 1/1966 | Korn | 62/3 |
| 3,234,595 | 2/1966 | Weichselbaum et al. | 62/3 |
| 3,308,633 | 3/1967 | Kritzer, Jr. | 165/48 |
| 3,314,242 | 4/1967 | Lefferts | 62/3 |
| 3,402,561 | 9/1968 | Mahoney | 62/3 |
| 3,481,154 | 12/1969 | Johnson | 165/48 |
| 3,712,072 | 1/1973 | Hoge et al. | 62/3 |
| 3,858,106 | 12/1974 | Launius | 62/3 |

Primary Examiner—Lloyd L. King
Attorney, Agent, or Firm—Gordon W. Hueschen

[57] ABSTRACT

This invention relates to a dental desk unit, having a cold plate for keeping amalgam and like material cold and to delay set-up thereof, and a hot section, having a hot plate to keep instruments or other materials at or near body temperature, and a plurality of wells to keep novocaine (procaine or procaine hydrochloride) and the like at or near body temperature.

19 Claims, 4 Drawing Figures

U.S. Patent
May 30, 1978
4,092,138
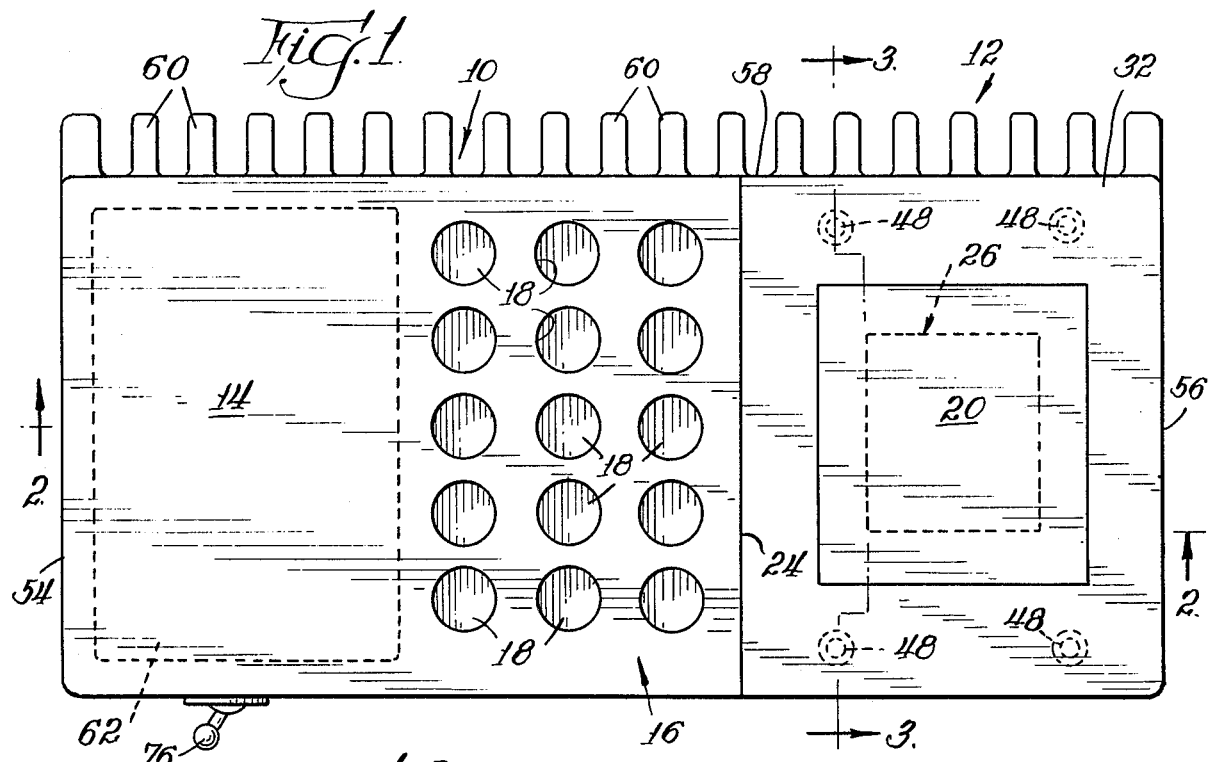
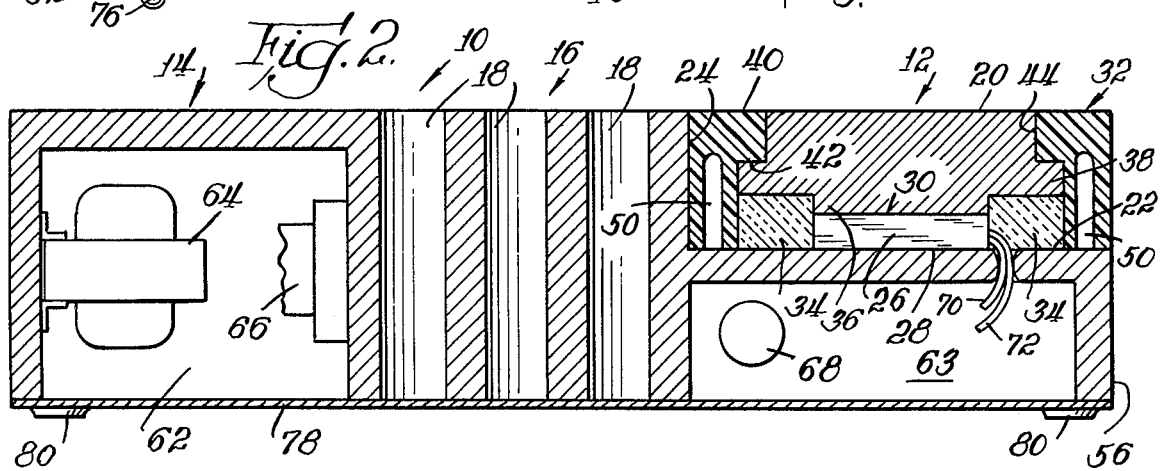
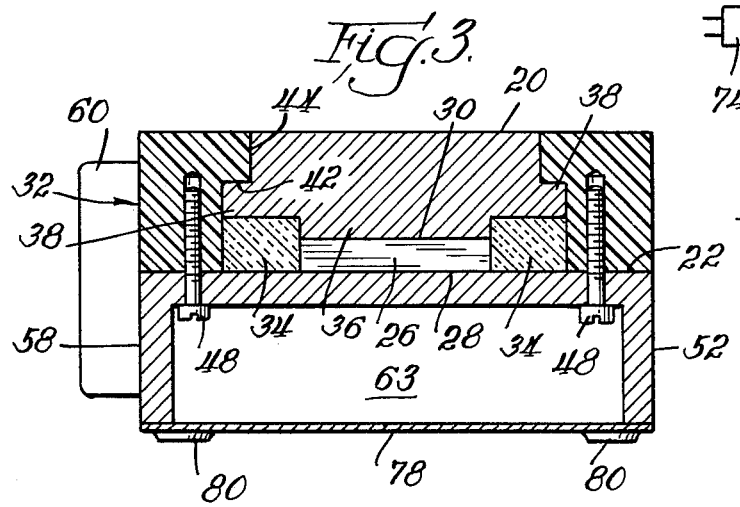
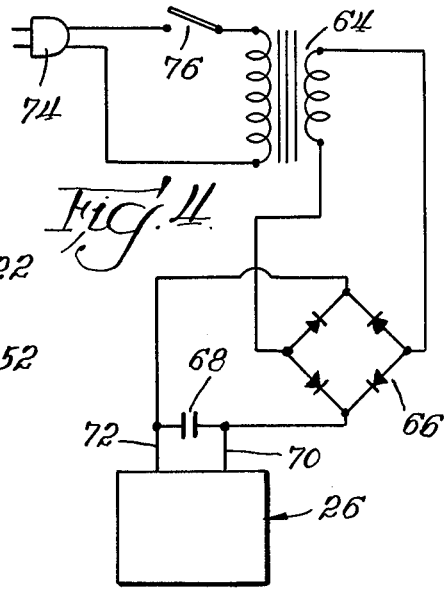

DENTAL DESK UNIT

BACKGROUND OF THE INVENTION

1. Field of Invention

This invention relates relates to a dental desk unit adapted to keep materials and tools used by the dentist at a temperature most suited to their use.

2. Prior Art

The need for keeping certain dental cements or filling material cooled to prevent premature setup is well recognized in the art, and suitable devices have been proposed for this purpose, as may be seen in U.S. Pat. Nos. 3,230,723 and 3,712,072, both of which utilize the well-known Peltier effect to obtain the desired cooling. Thermoelectric units of the Peltier type are well-known in the art. They comprise surfaces bonded together in such a way that, when a direct current is impressed on the element, one of the surfaces becomes hot, and the other surface becomes cold. In the devices of the references, the cold surface is utilized to provide the cooling of the device, and the heat generated by the hot surface is dissipated by a fan blowing on fins or other heat-radiating configurations. From the need for dissipating the heat with a fan, it is evident that the amount of heat generated is considerable, and is considered a disadvantage.

It has been proposed before to construct devices utilizing thermoelectric elements of the Peltier type, which utilize both the heat and cooling effect of the element. Such utilization is seen in U.S. Pat. Nos. 2,943,452 and 3,408,481. These devices, apart from their size and cumbersomeness, are not adapted for use as desk units in dentist's offices. They utilize closed compartments to conserve heat and to obtain as much cooling as possible, whereas these ends are not desirable in a dental desk unit, and without them, the references have no way of adequately balancing the heat and cooling obtained by the thermoelectric element.

U.S Pat. No. 3,808,825 discloses a device which purportedly accomplishes both cooling and heating by means of a thermoelectric element. Aside from the fact that the device is of questionable operativeness, because of the character of thermoelectric module, the two cups are of similar size, which means that the hot one would become extremely hot, and therefore be unsuitable for dental purposes. Moreover, the thermoelectric units are so constructed as to require cups of special shape, and therefore would have limited utility or none at all, if such specially shaped cups were not available.

OBJECTS OF THE INVENTION

It is an object of the invention to provide a new and useful dental desk unit. It is a further object of the invention to provide a dental desk unit having both heating and cooling capacity. It is a further object of the invention to provide a dental desk unit having a heating and cooling capacity properly balanced to obtain the desired cooling and heating effect. It is a further object of the invention to provide such a dental desk unit in which the desired heating and cooling is effected without the requirement of control means, such as thermostats and/or forced air blowers. It is an object of the invention to provide a dental desk unit having heating and cooling capacities which are automatically set without any controls, and without any change in air flow, forced or otherwise. It is an further object of the invention to avoid the disadvantages of the prior art and to obtain such advantages as will appear as the description proceeds.

SUMMARY OF THE INVENTION

The invention relates to a dental desk unit comprising a hot section of heat conducting material, a cold section of heat conducting material, insulating material separating said hot and cold sections and a thermoelectric unit of the Pelier type having a hot face and a cold face, said thermoelectric unit being imbedded in said insulating material with its hot face in heat transfer contact with said hot section and its cold face in heat transfer contact with said cold section. Advantageously, the unit has a hot plate exposed to the ambient atmosphere and a cold plate exposed to the ambient atmosphere which perferably are coplanar and, if desired, the unit has heat radiating fins and/or surfaces also exposed to the ambient atmosphere whereby the temperature of the hot plate and that of the cold plate are automatically determined for any given thermoelectric unit by the amount of surface exposed to the ambient atmosphere and by the voltage applied to the unit.

Advantageously, the desk unit of the invention has a plurality of vial-holding wells therein suitable for holding vials of novocaine or the like to keep the novocaine at the desired temperature. These wells advantageously are located between the hot and cold plates.

The thermoelectric unit is energized by means of a power pack which comprises a transformer, a rectifier, and a condenser and, if desired, a choke coil. Power packs of this character are well known in the art, and are utilized wherever a direct current, especially one of relatively low EMF, is required. Such power pack may be external, in which case the unit will be provided with a plug-in jack for connecting it to the external power pack. Advantageously, however, the power pack is made to fit within the device and, for this purpose, recesses are formed beneath the hot plate and, if desired, elsewhere in the hot section of the device. As some of the elements of the power pack, mainly the transformer and the rectifier, generate heat, it is desirable to have them located in a recess beneath the hot plate of the unit, and to adjust the radiating surfaces of the unit including any radiating fins employed, to dissipate whatever amount of heat is necessary in order to maintain the hot plate and the vial-holding wells at the desired temperature.

Advantageously, the outer portion of the insulating material separating the hot section and the cold section is made up of a rigid plastic material, and the inner section, which surrounds or encompasses the thermoelectric element is made up of an insulating material having a lower K factor than the rigid plastic material. Polystyrene foam and especially polyurethane foam have K factors in the order of $0.02 \pm 0.005$ BTU/hr/sq. ft/deg. F/hr and are particularly suitable for this purpose.

Advantageously, the hot section has a flat top face, and a flat lower face connected to the flat top face by a vertical wall. The effect of such a structure is that of a step with one of the surfaces higher than the other, the vertical wall being the riser between the two surfaces. The lower flat face is utilized as a base for the hot face of the thermoelectric unit and the heat generated by that face is conducted through the heat-conducting material of the hot section to the hot plate and the vial-holding wells. The cold section then, rests on the cold face of the thermoelectric unit and is held in heat-transfer contact therewith by means of the insulating material separating it from the hot section and enclosing the thermoelectric unit. Advantageously, the cold section has a portion of the same size and shape as the cold face of the thermoelectric unit, then a shoulder projecting outwardly toward the vertical wall and toward the edges of the lower flat face of the hot section. The cold section is completely surrounded by insulating material, the outer portion of which is plastic material and the inner portion of which is insulating material of a lower K factor. The shoulder extends outwardly to the plastic material, and the plastic material overhangs the shoulder so that when the plastic material is fastened to the lower flat face, the overhang of the plastic material presses down on the shoulder and forces the cold section into heat-transfer contact with the cold face of the thermoelectric element and, in turn, the hot face of the thermoelectric element into heat-transfer contact with the lower flat face. The space between the shoulder and the plastic material and the thermoelectric element is filled with the plastic material of a lower K factor. If desired, the plastic material may have pockets or voids in it at suitable intervals to increase its insulating properties.

Advantageously, the hot section is made as a unitary block of heat-conducting material, for example, aluminum. The cold section similarly is constructed of heat conducting material as a unitary block. The size and shape of the cold section is so coordinated with the plastic material, which is like a collar sealed on the lower face of the hot section so that the plastic material is, in effect, a continuation of the block of which the hot section is composed.

So constructed, there is provided a desk unit which provides hot and cold surfaces and vial-holding wells in which a functional balance is maintained between the cold and hot sections simply by exposing them to the ambient atmosphere.

BRIEF DESCRIPTION OF THE DRAWINGS

In the drawings,

FIG. 1 is a plan view of a dental desk unit according to the invention,

FIG. 2 is a cross-section taken along lines 2—2 of FIG. 1,

FIG. 3 is a cross-section taken along lines 3—3 of FIG. 1, and FIG. 4 is a schematic drawing of the power pack.

DETAILED DESCRIPTION OF THE INVENTION

In the modification shown in FIGS. 1, 2, and 3, the dental desk unit comprises a hot section 10 and a cold section 12. The hot section 10 comprises a hot plate 14 and a well section 16 containing a plurality of vial-holding wells 18. The cold section comprises a cold plate 20 which is coplanar with the hot plate 14 and the well section 16.

The hot section comprises an upper flat face 14–16 and a lower flat face 22 which is connected to the upper flat face by a vertical wall 24. The upper and lower flat faces lie in horizontal parallel planes.

Resting on the lower flat face 22 is a thermoelectric module or element 26. This module is of the well-known Peltier type, having a hot face 28 and a cold face 30, and is constructed in such a way that the impressing of a direct current EMF across the two faces causes the cold face to become cold and the hot face to become hot. The two faces are parallel, and flat. The hot face 28 rests on the lower flat face 22 of the hot section, and is in heat-transfer contact therewith. The cold plate 20 rests on the cold face 30 of the thermoelectric unit, and is in heat-transfer contact therewith.

The cold section 12 is separated from the hot section 10 by insulating material comprising a plastic collar 32, and insulating material 34, which has a lower K value.

The plastic material 24 may comprise any rigid plastic and suitably may be polyurethane, polycarbonate, nylon, polypropylene, or polystyrene. This plastic collar has the same size and shape as the lower flat face 22, and has the same height as the vertical wall 24. The top of the collar is flat, and lies in the plane of the upper flat face 14–16.

The insulating material 34 may be a plastic foam, such as polyurethane or polystyrene foam, having a low K factor. The purpose of this insulating material is to minimize heat transfer from the hot face 28 to the cold plate 20 of the thermoelectric element, and for that reason insulating material having a low coefficient of heat transfer is employed. Polyurethane foams, especially the Freon-blown polyurethane rigid foams, are well-recognized in the art as having a most advantageously low coefficient of heat-transfer and are most suitably employed as the insulating material 34.

The bottom of the cold plate 20 has a portion 36 which has essentially the same shape and size as the cold face 30 of the thermoelectric unit, and extends upwardly therefrom a substantial distance. Optimally, the portion 36 has the same size as the cold face 30, but desirably, may be slightly larger to insure against misalignment during assembly. This allows the insulating material 34 to extend well above the interface between the cold plate 20 and the cold face of the thermoelectric unit, thereby more effectively to prevent transfer of heat from the hot face 28 to the cold plate 20.

Projecting laterally from the top of the portion 36 is a shoulder 38 which extends laterally over the top of the insulating material 34 to the plastic collar 32, which has a shoulder 40 overlying the top 42 of the shoulder 38. The top portion 44 of the cold plate 20 abuts the shoulder 40 so as to provide an essentially hairline crack between the cold plate 20 and the plastic collar 32. Sometimes it is of advantage to have the cold plate either slightly above or slightly below the top surface of the collar 32.

The plastic collar 32 is bolted to the lower flat face 22 by bolts 48 or secured thereto by other suitable fastening means. The proportions are such that the shoulder 40 of the plastic collar 32 rests on the top face 42 of the shoulder 38 of the cold section 12 and thus forces the cold section 12 into heat-transfer contact with the cold face 30 of the thermoelectric unit and, in turn, the hot face 28 of the thermoelectric unit into heat transfer contact with the lower flat face 22 of the hot section 10.

If desired, the plastic collar 32 may have voids or pockets 50 in order to lower the heat-transfer coefficient of the plastic material. These pockets may be spaced regularly about the periphery of the collar 32, and will constitute dead air spaces between the cold section 12 and the vertical wall 24 and the ambient atmosphere on the other sides of the collar.

The hot section is made of a unitary block of heat-conducting material, preferably aluminum or like material, having a high coefficient of heat transfer. The block has a flat upper face 14–16, and a flat lower face 22, as previously described, and depending from these faces and normal thereto are front, side, and back walls 52, 54, 56 and 58 respectively. The rear 58 has radiating fins 60 for the purpose of helping to dissipate the heat from the hot section 10 and thus to regulate the temperature thereof.

Beneath the hot plate 14 is a recess 62 of a size and capacity to house the transformer 64 and rectifier 66 of the power pack illustrated in FIG. 4. The heat generated by these power pack elements is thus added to the hot section 10 at a point remote from the thermoelectric element 26, and thus tends to equalize the heat distribution throughout the hot section 10.

Beneath the lower flat face 22 is a second recess 63 in which may be housed the condenser 68 of the power pack and other elements thereof as desired. It is to be understood that the lead lines 70 and 72 are connected to the condenser 68 and the rectifier 66, which in turn is connected to the transformer 64 as shown in FIG. 4. The transformer in turn is connected to a line plug 74 through the cutoff switch 76 in a side wall of recess 62.

The recesses 62 and 63 also serve to reduce the weight of the unit, a result which can be further enhanced by having the small recess 63 extend through the vial-holding well section 16 to the larger recess 64.

The vial-holding wells 18 may be simple bores made into the hot section 10. If desired, they may extend all the way to the bottom of the hot section 10, in which case the bottom member 78, which closes the recesses 62 and 63, will also form the bottoms of the wells 18. The bottom 78 may be provided with cushioning pads 80 at the four corners of the unit.

It will thus be seen that the desk unit of the invention comprises a rectangular box-shaped unit having a flat top portion which comprises the hot plate 14 and the cold plate 20, and intermediately disposed well section 16 having a plurality of vial-holding wells 18 therein. Thus the cold section 12 has a top, front, sides or ends, and a back. Similarly, the cold plate 20 is exposed to the ambient atmosphere. There is thus obtained a functional balance between the heat input through the cold face 20 and the heat output through the radiating surfaces of the hot section, so as to obtain adequate cooling of the cold face 20 for the purpose intended, that is, of delaying the setting up of dental cements and filling materials, and at the same time, maintain a temperature in the hot section so that vials of novocaine or the like placed in the wells 18 will be maintained essentially at the desired temperature.

The thermoelectric elements used in the units are well known in the art. Generally, they are made up of a plurality of electrically connected P-N type crystals and faced with electrical insulating material which may be an epoxy resin, or, more desirably, a heat conducting ceramic material. If desired, heat transfer can be promoted by coating these faces with a heat conducting grease, for example, a silicone grease.

It is to be understood that the invention is not to be limited to the exact details of operation or materials of construction shown and described as obvious variations and equivalents will be apparent to one skilled in the art.

I claim:

1. A dental desk unit comprising a hot section of heat-conducting material, a cold section of heat-conducting material, insulating material separating said hot and cold sections, and a thermoelectric unit of the Peltier type having a hot face and a cold face, said thermoelectric unit being imbedded in said insulating material with its hot face in heat-transfer contact with said hot section and its cold face in heat-transfer contact with said cold section, wherein said hot section has an upwardly-facing, horizontally-disposed hot plate exposed to the ambient atmosphere and a substantial mass of said heat-conducting material between said hot plate and the hot face of said thermoelectric unit, wherein the thermoelectric element is energized by a self-contained power pack comprising a transformer, a rectifier, and a condenser, wherein the hot section has a recess beneath the hot plate thereof, wherein the heat-generating elements of said power pack are located in said recess, and wherein said hot face is separated from said recess by said heat-conducting material whereby the heat generated by the heat-conducting elements is conducted from said recess to said hot face.

2. A dental desk unit comprising a hot section of heat-conducting material, a cold section of heat-conducting material, insulating material separating said hot and cold sections, and a thermoelectric unit of the Peltier type having a hot face and a cold face, said thermoelectric unit being imbedded in said insulating material with its hot face in heat-transfer contact with said hot section and its cold face in heat-transfer contact with said cold section, wherein the hot section has a flat top face and a flat lower face connected to said flat top face by a vertical wall, and wherein the hot face of said element rests on and is in heat-transfer contact with said lower flat face, and wherein the cold section rests on, and is in heat-transfer contact with the cold face of said element.

3. The unit of claim 2, wherein the cold section has a flat top face which is coplanar with the flat top face of the hot section.

4. The unit of claim 3, wherein the cold section has a cross-section smaller than that of said lower flat face with its edges spaced inwardly of the edges of said lower flat face, and with the space between said edges being occupied by said insulating material.

5. The unit of claim 4, wherein the outside portion of said insulating material is of rigid plastic material, and the inside portion, which encases said thermoelectric unit, is of insulating material having a lower K factor.

6. The unit of claim 2, wherein the hot section has a plurality of vial-holding wells adjacent the vertical wall.

7. The unit of claim 3, in which the flat top face of said hot section has a plurality of vial-holding wells in the portion thereof adjacent the vertical wall.

8. The unit of claim 7, wherein the flat top face of said hot section comprises the portion having wells therein, and a flat hot plate portion which are exposed to the ambient atmosphere.

9. The unit of claim 8, wherein the hot section has a recess beneath said flat hot plate portion, and a smaller recesses beneath said lower, flat surface, and a self-contained power pack, the elements of which are housed in said recesses.

10. The unit of claim 9, wherein the elements of said power pack which generate heat are housed in the larger recess.

11. The unit of claim 5, wherein the cold section has a bottom portion which has essentially the size and shape of the cold face of said thermoelectric unit, has an outwardly projecting shoulder which projects out over said insulating material having a lower K value than said plastic material, and under an inwardly projecting shoulder of said plastic material.

12. The unit of claim 11, wherein the plastic material is secured to said lower flat face, and the proportions are such that the inwardly projecting shoulder of said plastic material engages the outwardly projecting shoulder of said cold section, and forces the cold section down and into heat-transfer contact with the cold face of the thermoelectric element, and the hot face of the thermoelectric element into heat-transfer contact with the lower flat face of said hot section.

13. The unit of claim 2, wherein the cold section comprises a unitary block of heat-conducting material, all parts of which are in heat-transfer with said hot face, and wherein the major portion of the outer surface of said block is exposed to the ambient atmosphere.

14. The unit of claim 13, wherein the unitary block has laterally projecting, radiating fins.

15. The unit of claim 13, wherein the cold section has a cross-section smaller than that of said lower flat face with its edges spaced inwardly of the edges of said lower flat face, and with the space between said edges being occupied by said insulating material, and wherein said hot and cold sections have flat top faces which lie in a common plane, the flat top face of said cold section comprising a cold plate which is surrounded by and separated from the flat top face of said hot section by said insulating material.

16. The unit of claim 15, wherein the portion of said insulating material which surrounds said cold plate and separates it from the flat top face of said hot section is of rigid plastic material, and the portion which encases said thermoelectric unit is of insulating material having a lower K factor than said rigid plastic material.

17. The unit of claim 16, wherein the cold section has a bottom portion which has essentially the size and shape of the cold face of said thermoelectric unit, has an outwardly projecting shoulder which projects out over said insulating material having a lower K value to said plastic material, and under an inwardly projecting shoulder of said plastic material.

18. The unit of claim 17, wherein the plastic material is secured to said lower flat face, and the proportions are such that the inwardly projecting shoulder of said plastic material engages the outwardly projecting shoulder of said cold section, and forces the cold section down and into heat-transfer contact with the cold face of the thermoelectric element, and the hot face of the thermoelectric element into heat-transfer contact with the lower flat face of said hot section.

19. The unit of claim 18, wherein the plastic material rests on said lower flat surface, has the same width and breadth as the lower flat surface, and has the same height as said vertical wall.

* * * * *